(12) United States Patent
Scholz et al.

(10) Patent No.: US 9,777,407 B2
(45) Date of Patent: Oct. 3, 2017

(54) HYDROPHILIC POLYPROYLENE MELT ADDITIVES

(75) Inventors: Matthew T. Scholz, Woodbury, MN (US); Michael R. Berrigan, Oakdale, MN (US); Thomas P. Klun, Lakeland, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 351 days.

(21) Appl. No.: 13/260,589

(22) PCT Filed: Mar. 25, 2010

(86) PCT No.: PCT/US2010/028665
§ 371 (c)(1),
(2), (4) Date: Dec. 7, 2011

(87) PCT Pub. No.: WO2010/111491
PCT Pub. Date: Sep. 30, 2010

(65) Prior Publication Data
US 2012/0077886 A1  Mar. 29, 2012

Related U.S. Application Data

(60) Provisional application No. 61/164,247, filed on Mar. 27, 2009.

(51) Int. Cl.
| | | |
|---|---|---|
| *D01F 6/06* | (2006.01) | |
| *A61L 15/24* | (2006.01) | |
| *A61L 15/48* | (2006.01) | |
| *A61L 31/04* | (2006.01) | |
| *A61L 31/14* | (2006.01) | |
| *D01F 1/10* | (2006.01) | |

(52) U.S. Cl.
CPC .............. *D01F 6/06* (2013.01); *A61L 15/24* (2013.01); *A61L 15/48* (2013.01); *A61L 31/048* (2013.01); *A61L 31/14* (2013.01); *D01F 1/10* (2013.01)

(58) Field of Classification Search
None
See application file for complete search history.

(56) References Cited

U.S. PATENT DOCUMENTS

| | | |
|---|---|---|
| 2,462,331 A | 2/1949 | Myers |
| 2,723,999 A | 11/1955 | Cowen |
| 2,732,398 A | 1/1956 | Brice |
| 2,915,554 A | 12/1959 | Ahlbrecht |
| RE24,906 E | 12/1960 | Ulrich |
| 3,048,263 A | 8/1962 | Sacks |
| 3,048,266 A | 8/1962 | Hackhel |
| 3,285,855 A | 11/1966 | Dexter |
| 3,389,827 A | 6/1968 | Abere |
| 3,489,148 A | 1/1970 | Duncan |
| 3,565,985 A | 2/1971 | Schrenk |
| 3,592,194 A | 7/1971 | Duncan |
| 3,644,482 A | 2/1972 | Dexter |
| 3,692,618 A | 9/1972 | Dorschner |
| 3,787,351 A | 1/1974 | Olson |
| 3,809,077 A | 5/1974 | Hansen |
| RE28,102 E | 8/1974 | Mayhew |
| 3,847,676 A | 11/1974 | Palmer |
| 3,849,241 A | 11/1974 | Butin |
| 3,860,003 A | 1/1975 | Buell |
| 3,871,378 A | 3/1975 | Duncan |
| 3,971,373 A | 7/1976 | Braun |
| 3,973,068 A | 8/1976 | Weber |
| 4,002,775 A | 1/1977 | Kabara |
| 4,067,997 A | 1/1978 | Kabara |
| 4,073,852 A | 2/1978 | Mesek |
| 4,076,698 A | 2/1978 | Anderson |
| 4,100,324 A | 7/1978 | Anderson |
| 4,112,213 A | 9/1978 | Waldman |
| 4,181,762 A | 1/1980 | Benedyk |
| 4,189,420 A | 2/1980 | Sugimoto |
| 4,258,097 A | 3/1981 | Benedyk |
| 4,273,802 A | 6/1981 | Kamada |
| 4,273,892 A | 6/1981 | Rave |
| 4,274,971 A | 6/1981 | Hartinger |
| 4,293,460 A | 10/1981 | Marshall |
| 4,296,165 A | 10/1981 | Kakar |
| 4,307,143 A | 12/1981 | Meitner |
| 4,310,509 A | 1/1982 | Berglund |
| 4,323,557 A | 4/1982 | Rosso |
| 4,324,246 A | 4/1982 | Mullane |
| 4,340,563 A | 7/1982 | Appel |
| 4,363,891 A | 12/1982 | Rosen |
| 4,426,477 A | 1/1984 | Yasumatsu |
| 4,429,001 A | 1/1984 | Kolpin |
| 4,522,203 A | 6/1985 | Mays |

(Continued)

FOREIGN PATENT DOCUMENTS

| | | |
|---|---|---|
| CS | 253 423 | 10/1988 |
| EP | 0 109126 | 5/1984 |

(Continued)

OTHER PUBLICATIONS

AATCC Test Method 100-1993 "Antibacterial Finishes on Textile Materials: Assessment of"; AATCC Technical Manual, 1997, pp. 143-144.

AATCC Test Method 118-1983, "Oil Repellency: Hydrocarbon Resistance Test"; AATC Technical Manual, vol. 61, 1986, pp. 195.

ASTM F719-81 (Reapproved 2007) e, "Standard Practice for Testing Biomaterials in Rabbits for Primary Skin Irritation", 2007, 3 pages.

ASTM F763-04 (Reapproved 2010), "Standard Practice for Short-Term Screening of Implant Materials"; 2010, 4 pages.

Kabara, "Antimicrobial Lipids: Natural and Synthetic Fatty Acids and Monoglycerides," Antimicrobial Lipids, Sep. 1977, vol. 12, No. 9, pp. 753-759.

(Continued)

*Primary Examiner* — Craig Ricci

(57) ABSTRACT

Melt additive ionic and non-ionic surfactants to impart stable durable hydrophilicity to thermoplastic polymers or blends thereof.

14 Claims, 2 Drawing Sheets

(56) References Cited

U.S. PATENT DOCUMENTS

| | | |
|---|---|---|
| 4,540,730 A | 9/1985 | Kieser |
| 4,561,435 A | 12/1985 | McKnight |
| 4,565,743 A | 1/1986 | Akao |
| 4,565,843 A | 1/1986 | Dunwald |
| 4,578,414 A | 3/1986 | Sawyer |
| 4,581,397 A | 4/1986 | Witman |
| 4,589,876 A | 5/1986 | Van Tilburg |
| 4,598,004 A | 7/1986 | Heinecke |
| 4,615,937 A | 10/1986 | Bouchette |
| 4,648,876 A | 3/1987 | Becker |
| 4,726,989 A | 2/1988 | Mrozinski |
| 4,734,448 A | 3/1988 | Kasahara |
| 4,737,410 A | 4/1988 | Kanter |
| 4,762,873 A | 8/1988 | Miyauchi |
| 4,840,738 A | 6/1989 | Hardy |
| 4,857,251 A | 8/1989 | Nohr |
| 4,902,553 A | 2/1990 | Hwang |
| 4,906,687 A | 3/1990 | Modic |
| 4,920,168 A | 4/1990 | Nohr |
| 4,923,914 A | 5/1990 | Nohr |
| 4,933,229 A | 6/1990 | Insley |
| 5,034,008 A | 7/1991 | Breitkopf |
| 5,057,262 A | 10/1991 | Nohr |
| 5,064,578 A | 11/1991 | Insley |
| 5,087,520 A | 2/1992 | Suzuki |
| 5,120,888 A | 6/1992 | Nohr |
| 5,145,727 A | 9/1992 | Potts |
| 5,149,576 A | 9/1992 | Potts |
| 5,208,257 A | 5/1993 | Kabara |
| 5,244,724 A | 9/1993 | Antonacci |
| 5,244,951 A | 9/1993 | Gardiner |
| 5,268,733 A | 12/1993 | Wright |
| 5,300,357 A | 4/1994 | Gardiner |
| 5,320,772 A | 6/1994 | Tricca |
| 5,346,944 A | 9/1994 | Hayashida |
| 5,362,555 A | 11/1994 | Lal |
| 5,389,374 A | 2/1995 | Brown-Skrobot |
| 5,427,842 A | 6/1995 | Bland |
| 5,460,833 A | 10/1995 | Andrews |
| 5,569,461 A | 10/1996 | Andrews |
| 5,589,122 A | 12/1996 | Leonard |
| 5,599,602 A | 2/1997 | Leonard |
| 5,614,574 A | 3/1997 | Sheth |
| 5,618,614 A | 4/1997 | Nohr |
| 5,629,376 A | 5/1997 | Sargent |
| 5,648,166 A | 7/1997 | Dunshee |
| 5,654,086 A * | 8/1997 | Nishijima et al. ............ 442/199 |
| 5,660,922 A | 8/1997 | Herridge |
| 5,753,252 A | 5/1998 | Brown-Skrobot |
| 5,763,335 A | 6/1998 | Hermann |
| 5,804,625 A * | 9/1998 | Temperante et al. ......... 524/188 |
| 5,817,325 A | 10/1998 | Sawan |
| 5,849,843 A | 12/1998 | Laurin |
| 5,854,147 A | 12/1998 | Nohr |
| 5,876,840 A | 3/1999 | Ning |
| 5,882,357 A | 3/1999 | Sun |
| 5,910,368 A | 6/1999 | Ehret |
| 5,951,993 A | 9/1999 | Scholz |
| 6,033,705 A | 3/2000 | Isaacs |
| 6,071,541 A | 6/2000 | Murad |
| 6,083,602 A | 7/2000 | Caldwell |
| 6,297,301 B1 | 10/2001 | Erderly |
| 6,316,019 B1 | 11/2001 | Yang |
| 6,380,289 B1 | 4/2002 | Thompson, Jr. |
| 6,436,855 B1 | 8/2002 | Iwata |
| 6,451,713 B1 | 9/2002 | Tay |
| 6,482,341 B1 | 11/2002 | Jongboom |
| 6,762,339 B1 | 7/2004 | Klun |
| 6,916,752 B2 | 7/2005 | Berrigan |
| 7,230,043 B2 | 6/2007 | Klun |
| 7,258,921 B2 * | 8/2007 | Hashiba et al. ............ 428/402 |
| 8,721,943 B2 | 5/2014 | Moore et al. |
| 8,858,986 B2 | 10/2014 | Scholz et al. |
| 8,932,704 B2 | 1/2015 | Porbeni et al. |
| 2004/0024141 A1 | 2/2004 | Hasebe |
| 2004/0241216 A1 | 12/2004 | Klun |
| 2008/0142023 A1 | 6/2008 | Schmid |
| 2008/0200890 A1 | 8/2008 | Wood |
| 2009/0105679 A1 * | 4/2009 | Joubert et al. ........... 604/385.01 |
| 2011/0117176 A1 | 5/2011 | Klun |
| 2011/0151737 A1 | 6/2011 | Moore et al. |
| 2011/0189463 A1 | 8/2011 | Moore et al. |
| 2012/0088424 A1 | 4/2012 | Eric et al. |
| 2012/0315225 A1 | 12/2012 | Porbeni et al. |
| 2013/0190408 A1 | 7/2013 | Scholz et al. |
| 2013/0288556 A1 | 10/2013 | Moore et al. |
| 2014/0210141 A1 | 7/2014 | Moore et al. |
| 2015/0004866 A1 | 1/2015 | Scholz et al. |

FOREIGN PATENT DOCUMENTS

| | | | |
|---|---|---|---|
| EP | 0 161 757 | 11/1985 | |
| EP | 0 395 099 | 10/1990 | |
| EP | 0 394028 | 10/1990 | |
| EP | 0 455 370 | 11/1991 | |
| EP | 0 456 044 | 11/1991 | |
| EP | 0 516 271 | 12/1991 | |
| EP | 0 617938 | 10/1994 | |
| EP | 0 674891 | 10/1995 | |
| EP | 0 937812 | 8/1999 | |
| GB | 941757 | 11/1963 | |
| GB | 2282 817 | 4/1995 | |
| GB | 2323784 | 7/1998 | |
| JP | 57-8236 | 1/1982 | |
| JP | 58-023920 | 2/1983 | |
| JP | 59-163477 | 9/1984 | |
| JP | 60-44539 | 3/1985 | |
| JP | 60-58444 | 4/1985 | |
| JP | 60-28869 | 7/1985 | |
| JP | 64-6173 | 1/1989 | |
| JP | 4-020571 | 1/1992 | |
| JP | 4-253752 | 9/1992 | |
| JP | 4-328138 | 11/1992 | |
| JP | 5-112660 | 5/1993 | |
| JP | 5-125220 | 5/1993 | |
| JP | 07-000444 | 1/1995 | |
| JP | 2657998 | 9/1997 | |
| JP | 10-168757 | 6/1998 | |
| JP | 2830371 | 12/1998 | |
| JP | 11-043405 | 2/1999 | |
| JP | 11-113779 | 4/1999 | |
| JP | 11-113780 | 4/1999 | |
| JP | 2005-509734 | 4/2005 | |
| JP | 48-13737 | 11/2011 | |
| LU | 85156 | 9/1985 | |
| WO | WO 92-18569 | 10/1992 | |
| WO | WO 93-20790 | 10/1993 | |
| WO | WO 95-01396 | 1/1995 | |
| WO | WO 97-11912 | 4/1997 | |
| WO | WO 97-44508 | 11/1997 | |
| WO | WO 98-09520 | 3/1998 | |
| WO | WO 99-00447 | 1/1999 | |
| WO | WO 99-66793 | 12/1999 | |
| WO | WO 03/044153 | 5/2003 | |
| WO | WO 03-054260 | 7/2003 | |
| WO | WO 2006/097597 | * 9/2006 | ............ C08K 5/42 |
| WO | WO 2014/059239 | 4/2014 | |

OTHER PUBLICATIONS

Klun, "Hydrophilic Melt Additives: Synergistic Fluorochemical/Hydrocarbon Surfactant Mixtures," Proceedings of INDA-TEC '97, Cambridge, MA, Sep. 8-10, 1997, pp. 24.0-24.15.

Projan, "Glycerol Monolaurate Inhibits the Production of B-Lactamase, Toxic Shock Syndrome Toxin-1, and Other Staphylococcal Exoproteins by Interfering with Signal Transduction" Journal of Bacteriology, Jul. 1994, vol. 176, No. 14, pp. 4204-4209.

Wente, "Manufacture of Superfine Organic Fibers", Naval Research Laboratories, NRL Report No. 4364, May 25, 1954, 22 pages.

Wente, "Superfine Thermoplastic Fibers", Industrial and Engineering Chemistry, Aug. 1956; vol. 48, No. 8, 1342-1346.

International Search Report for PCT/US2010/28665, mailed May 20, 2010, 3 pages.

(56) References Cited

OTHER PUBLICATIONS

Written Opinion of PCT/US2010/28665, mailed May 20, 2010, 8 pages.
European Search Report for PCT/US2010-028665, Jul. 20, 2012, 5 pages.
U.S. Appl. No. 62/069,934, filed Oct. 29, 2014, Chakravarty et al.

* cited by examiner

HYDROPHILIC POLYPROYLENE MELT ADDITIVES

CROSS REFERENCE TO RELATED APPLICATIONS

This application is a national stage filing under 35 U.S.C. 371 of PCT/US2010/028665, filed Mar. 25, 2010, which claims priority to U.S. Provisional Application No. 61/164,247, filed Mar. 27, 2009, the disclosure of which is incorporated by reference in its/their entirety herein.

BACKGROUND OF THE INVENTION

Thermoplastic polymers are widely employed to create a variety of products, including blown and cascade films, extruded sheets, foams, fibers and products made therefrom, woven and knitted fabrics, and non-woven fibrous webs. Many thermoplastic polymers used in these products, such as polypropylene, are inherently hydrophobic, and there are a number of uses for thermoplastic polymers where their hydrophobic nature either limits their use or requires some effort to modify the surface of the shaped articles made therefrom. For example, polyolefins are used in the manufacture of nonwoven webs (that are employed in the construction of absorbent articles such as diapers, feminine care products, and personal incontinence products) and the use of such nonwoven webs are limited because of their hydrophobic nature. Polyolefins are particularly desirable for these applications because they are lower cost and provide a soft "hand" (e.g., a soft feel to the nonwoven web) due to the relatively low glass transition temperature.

Coating methods to provide a hydrophilic surface are known, but also have some limitations. The extra step required in coating preparation is expensive, time consuming and requires specialized equipment. Many of the solvents used for coating are flammable liquids or have exposure limits that require special production facilities. When coated out of aqueous solutions, the water must be subsequently removed in an oven, which is energy intensive and costly since water has a high heat of vaporization, causing line speeds to be slow. Furthermore, the quantity of any surfactant used to provide the hydrophilic surface is limited by the solubility in the coating solvent, the amount of the coating applied, and potential foaming problems.

WO 92/18569 and WO 95/01396 (Sargent et al.) describe fluorochemical additives for use in the extrusion of thermoplastic polymers to prepare films and fibers with anti-wetting (repellent) and antistatic properties.

The addition of one or more surfactants to the melts of thermoplastic polymers to impart hydrophilicity to both the surface and the bulk of the fiber is also known. U.S. Pat. Nos. 4,857,251 and 4,920,168 (Nohr et al.) describe a method of forming fibers by melt-extrusion of a surface-segregatable thermoplastic composition that comprises thermoplastic polymer and a siloxane-containing additive having certain moieties.

Fluorochemicals and/or fluoro-containing groups are also known to impart hydrophilicity to fibers. See, e.g., U.S. Pat. No. 5,804,625 (Temperante et al.); EP Patent No. 0 516271 (Gardiner); U.S. Pat. Nos. 5,244,951 and 5,300,357 (Gardiner) and U.S. Pat. No. 7,230,043 (Klun).

Other additives have also been described. U.S. Pat. No. 4,189,420 (Sugimoto) discloses surface wetting agents selected from polyethylene alkyl ethers, polyoxyethylene fatty acid esters, sorbitan fatty acid esters, sodium dialkylsulfosuccinate, mono- and diglycerides, as well as polyglycerol fatty acid esters. U.S. Pat. No. 5,087,520 (Suzuki et al.) describes fibers comprising a polyolefin or polyester having a mixture of a fatty acid diethanolamide, a polyether-modified silicone, a sorbitan fatty acid ester and a metal salt of an alkylsulfonate.

Certain classes of hydrocarbon, silicone, and fluorochemical surfactants have each been described as useful for imparting hydrophilicity to polymers. These surfactants typically are contacted with the thermoplastic polymer in one of two ways: (1) by topical application, e.g., spraying or padding or foaming, of the surfactants from aqueous solution to the extruded nonwoven web or fiber followed by drying, or (2) by incorporation of the surfactant into the polyolefin melt prior to extrusion of the web. The latter is more preferable but it is difficult to find a surfactant that will reliably bloom to the surface of the fiber or film in sufficient amount to impart hydrophilicity, and then remain properly oriented at the surface to ensure durable hydrophilicity. As previously described, webs made hydrophilic by topical application of a surfactant suffer many drawbacks. Some web constructions are reported to also have diminished hydrophilicity after a single contact with aqueous media.

Disadvantages to topical application of a surfactant to impart hydrophilicity, such as described above, can include skin irritation from the surfactant itself, non-uniform surface and bulk hydrophilicity. Incorporating one or more surfactants into the thermoplastic polymer as a melt additive alleviates the problems associated with topical application and in addition may provide a softer "hand" to the fabric or nonwoven web into which it is incorporated.

There continues to be a need to obtain durable wettability of polyolefin (e.g. polypropylene) fibrous nonwovens using melt additive surfactants that are nontoxic and preserve or improve the "hand" of the fabric.

SUMMARY OF THE INVENTION

The present invention is directed to a composition, article and method for making a durable hydrophilic, and preferably biocompatible, composition. The compositions incorporate particular ionic surfactants and non-ionic surfactants in combination as melt additives to impart stable, durable hydrophilicity to thermoplastic polymers. The compositions may be melt-processable and have utility in a variety of food safety, medical, personal care and water purification, and air and liquid filtration applications. Importantly, the compositions can be manufactured at a lower cost without compromising the physical properties of the polyolefin (e.g. tensile, elongation, etc.), allowing its use with low cost disposable fibrous products. The webs made with the fiber compositions described herein remain hydrophilic and water absorbent after repeated contact ("insult") with water, e.g. saturating with water, wringing out and allowing to dry.

Articles made with the durable hydrophilic composition can comprise molded polymeric articles, polymeric sheets, polymeric fibers, woven webs, nonwoven webs, porous membranes, polymeric foams, as well as layered compositions such as thermal or adhesive laminates, and combinations thereof made of the compositions described above. Such articles encompass both disposable and reusable articles. Examples of useful articles of this disclosure are wound contact materials made of a film, foam and/or woven or nonwoven comprising the durable hydrophilic composition; and surgical drapes or surgical gowns, as well as personal hygiene articles such as diapers, feminine hygiene pads and the like made of the durable hydrophilic composition.

The method of the present disclosure comprises providing the thermoplastic polymers and the surfactants as described herein, and blending these materials sufficiently to yield a biocompatible, durable hydrophilic composition.

In one aspect, the polymer composition is melt processable, such that the polymer composition is capable of being extruded. The melt processable composition of thermoplastic polymer and surfactants exhibits durable hydrophilicity.

In another aspect, the polymer composition is solvent soluble or dispersible and the composition may be solvent cast, solvent spun to form films or fibers, or foams.

For the following defined terms, these definitions shall be applied, unless a different definition is given in the claims or elsewhere in the specification.

The term "biocompatible" means the composition does not produce toxic, injurious or immunological response in or on living tissue when in contact with the tissue. Test methods used include ASTM F719 for applications where the compositions contact tissue (such as skin, wounds, or mucosal tissue including in an orifice such as the esophagus or urethra) and ASTM F763 for applications where the compositions are implanted in tissue.

The term "stable durable hydrophilicity" or "durably hydrophilic" means that the composition, typically in fiber or fabric form, remains water absorbent when aged at least 30 days at 23° C., and preferably at least 40 days at 23° C.

The term "polyolefin" as used herein means a polymer produced from a simple olefin (also called an alkene) as a monomer. An equivalent term is polyalkene. For example, polyethylene is the polyolefin produced by polymerizing the olefin ethylene. Polyolefins as used herein also include copolymers of olefinic monomers with nonolefinic monomers. Polyolefins also include polyalphaolefins The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The recitation of numerical ranges by endpoints includes all numbers subsumed within that range (e.g. 1 to 5 includes 1, 1.5, 2, 2.75, 3, 3.8, 4, and 5).

As used herein, "a," "an," "the," "at least one," and "one or more" are used interchangeably. The term "and/or" (if used) means one or all of the identified elements/features or a combination of any two or more of the identified elements/features.

The term "and/or" means one or all of the listed elements/features or a combination of any two or more of the listed elements/features.

The above summary is not intended to describe each embodiment or every implementation of the present invention. Rather, a more complete understanding of the invention will become apparent and appreciated by reference to the following Detailed Description of Exemplary Embodiments and claims.

BRIEF DESCRIPTION OF THE DRAWINGS

The invention will be further explained with reference to the drawing figures listed below, where like structure is referenced by like numerals throughout the several views.

DETAILED DESCRIPTION OF EXEMPLARY EMBODIMENTS

Figure 1:
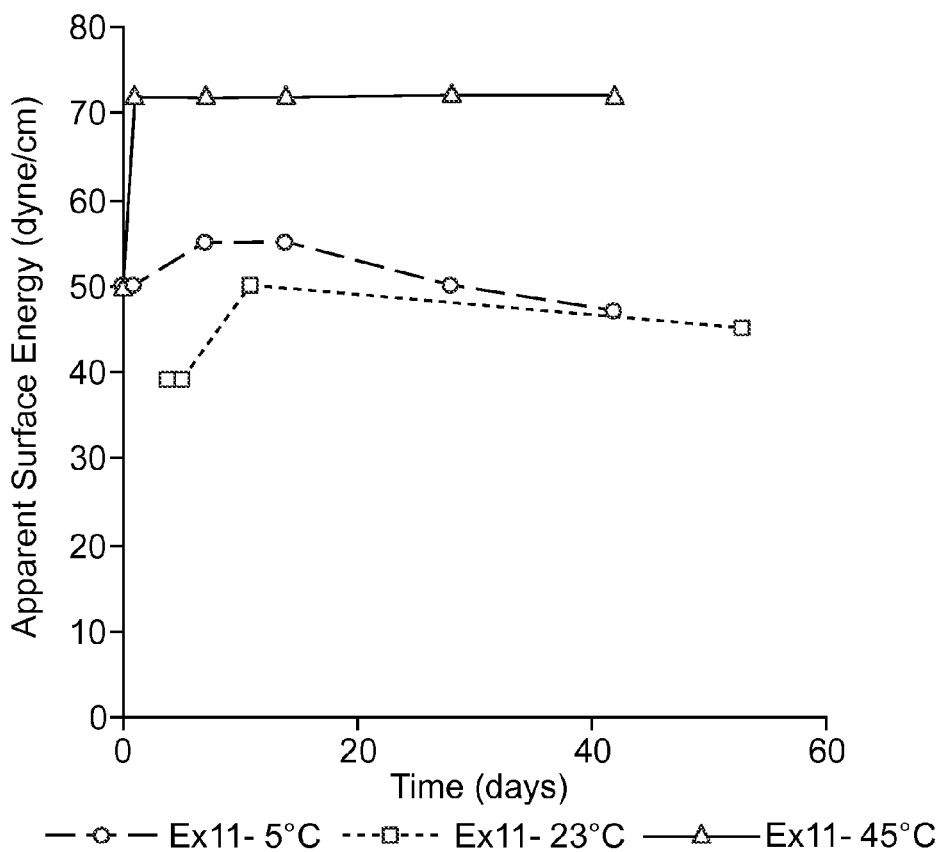
FIG. 1 is a graph that shows the data for apparent surface energy of an exemplary nonwoven composition as described herein.

The present invention discloses the use of melt additive ionic and non-ionic surfactants to impart stable durable hydrophilicity to thermoplastic polymers or blends thereof. Preferred thermoplastic polymers are polyolefins, including polypropylene, polyethylene, linear low density polyethylene, low density polyethylene, high density polyethylene, metallocene polyethylene, blends and copolymers thereof. In fiber form, the polyolefin fibers may be blended with other thermoplastic (e.g. polyester, nylon, acrylic, polyurethane, and the like) and non-thermoplastic fibers (including natural fibers such as cotton, wood pulp, rayon, jute, hemp, and the like). The compositions described herein are particularly useful for making hydrophilic absorbent nonwoven/film laminate drapes used in surgery, as well as personal care absorbents such as feminine hygiene pads, diapers, incontinence pads, and the like.

Hydrophilicity, or the lack thereof, can be measured in a variety of ways. For example, when water contacts a porous nonwoven web that is hydrophobic or has lost its hydrophilicity, the water does not flow, or flows undesirably slowly, through the web. Importantly the fibers and webs formed with the compositions described herein exhibit stable hydrophilicity (water absorbency). That is, they remain hydrophilic after aging in a clean but porous enclosure such as a poly/Tyvek pouch for over 30 days at 23° C. (or lower for certain applications) and preferably for over 40 days. Most preferred compositions remain stable and durably hydrophilic (water absorbent) after more than 10 days at 45° C., preferably more than 30 days at 45° C., and most preferably greater than 40 days at 45° C. when tested according to the methods described in the Examples. Preferred fibers are instantaneously wettable and absorbent and are capable of absorbing water at very high initial rates.

In one aspect, a durable hydrophilic, thermoplastic composition is provided comprising at least one thermoplastic polymer, (e.g., polypropylene, polyethylene, and the like as well as blends and copolymers thereof); one or more ionic surfactants selected from the group consisting of sulfate, sulfonate, sultaine, phosphate group-containing surfactants and combinations thereof; and one or more non-ionic surfactants selected from the group consisting of: (i) at least one non-ionic, non-fluorinated, polyoxyethylene-group-containing surfactants that contain between 5 and 80 weight percent polyoxyethylene; (ii) at least one non-ionic fluorochemical surfactant; and (iii) combinations of (i), (ii) and (iii). The composition then can be melt extruded to form a film or fiber. The blend of surfactant(s) is present in the film or fiber in an amount sufficient to impart durable hydrophilicity to the film or fiber at its surface.

In another aspect, durable hydrophilic films, durable hydrophilic fabrics, and webs constructed from said fibers, are provided. Articles made from durable hydrophilic fabrics and webs including medical drapes, wound dressings, medical gowns, aprons, filter media, industrial wipes and personal care and home care products such as diapers, facial tissue, facial wipes, wet wipes, dry wipes, disposable absorbent articles and garments such as infant diapers or training pants, adult incontinence products, feminine hygiene products such as sanitary napkins and panty liners and the like, are also described.

Antifog films are possible when transparent thermoplastic polymers are used. Antifog films may be used in food packaging, for safety eyewear and the like. Such films may be used alone or laminated to other substrates, including optically clear substrates.

In yet another aspect, multi-layer, aqueous liquid-absorbent articles comprising a backing sheet attached to the fiber (nonporous film) imperious to aqueous media. For example, importantly some surgical drapes are film/nonwoven laminates which are liquid impervious to prevent liquid that is absorbed into the fibrous top sheet from wicking through to the skin surface where it would be contaminated with bacteria present on the skin. In other embodiments the construction may further comprise an aqueous media permeable and optionally absorbent topsheet, and an aqueous liquid-absorbent (i.e., hydrophilic) layer constructed of the above-described web or fabric juxtaposed there between, useful in constructing for example, disposable diapers, wipes or towels, sanitary napkins, and incontinence pads.

The compositions of this invention are "relatively homogenous." That is they can be produced by melt extrusion with good mixing and at the time of extrusion would be relatively homogenous in concentration of additives such as surfactants throughout the fiber both longitudinally and radially. Obviously, longitudinal differences may occur due to varying the concentration of any of the additive(s). It is recognized, however, that over time and/or with heat treatment the surfactant(s) may migrate to become higher or lower in concentration at certain points such as at the surface of the fiber. The surfactants used in this invention may be employed in the sheath layer of sheath core fibers or in only certain layers of film-film and film-fabric laminates. Importantly, the surfactants are found throughout the layer in which they are present.

In another aspect, a method of preparing durable hydrophilic fibers from a mixture or blend of thermoplastic polymer, at least one ionic surfactant and at least one non-ionic surfactant is provided as further described herein. The melt of the blend is processed or shaped, for example, by extrusion or molding to produce fibers with the surfactants dissolved or dispersed within the fiber and at least partially present at the surfaces of the fiber to render those surfaces durably hydrophilic. Because some surfactants demonstrate thermal sensitivity, the processing temperatures in the extruder are preferably kept below about 300° C., and more preferably below about 250° C., where those surfactants are exposed to such temperatures given the particular processing technique.

The durable hydrophilicity is achieved without requiring post fiber chemical finishing operations, e.g. application of additional surfactant, because the fiber is durably hydrophilic as extruded, however, heating the web after extrusion may help to bloom surfactant to the surface and improve hydrophilicity. This is done at temperatures at or above the glass transition temperature of the thermoplastic and is typically less than 120° C., and more preferably less than 100° C. Blooming does not occur for all surfactants, and with some surfactants, heating of the web post-extrusion should be avoided to minimize possible degradation of the hydrophilic properties.

The hydrophilicity imparted to the fiber is done using at least one melt additive ionic surfactant and at least one melt additive non-ionic surfactant. These preferably are combined in specific ratios as discussed below. The surfactants are conveniently compounded with the polymer in a concentrate composition, which is mixed with virgin polymer in the hopper or elsewhere along the extruder, as long as blending is achieved to render a substantially uniform mixture. Alternatively, the combined surfactants may be added into the extruder directly (without precompounding), for example, using a positive displacement pump or weight loss feeder.

Preferred compositions of the claimed invention are free of glycerides. As used herein, "glycerides" means acyl esters of glycerin, including mono-, di-, and triglycerides, as well as mixtures thereof. For glycerides having more than one acyl group, the acyl groups may be of differing chain lengths (for example, a mixed glycerides disclosed in U.S. Pat. No. 4,189,420 (Sugimoto et al.)).

Preferred compositions of this invention include a relatively homogenous composition comprising at least one thermoplastic polymer, which is preferably polyolefin, and even more preferably, polypropylene or polyethylene. The thermoplastic polyolefin is preferably essentially free of perflourinated surfactants when formed by melt extrusion. In certain embodiments the compositions preferably include an enhancing amount of a second polyolefin polymer, hereinafter referred to as a "hydrophilic enhancing polyolefin". The hydrophilic enhancing polyolefin is typically derived from monomers having at least 4 hydrocarbons and generally has a molecular weight less than that of the thermoplastic polyolefin polymer. The preferred hydrophilic enhancing polyolefin is a polyalphaolefin, and more particularly, polybutylene.

Preferred compositions of this invention also comprise at least one ionic surfactant in an amount of 0.25 to 8 weight percent based on the total weight of the composition, more preferably an amount of 0.5 to 4 weight percent based on total weight of the composition, and even more preferably an amount of 0.75 to 2 weight percent of the composition. Also present is at least one non-ionic surfactant, present in preferred compositions in a concentration of 0.25 to 8 weight percent based on the total weight of the composition and more preferably an amount of 0.5 to 4 weight percent based on the total weight of the composition, and even more preferably an amount of 0.75 to 2 weight percent based on the total weight of the composition. The ratio of the ionic and non-ionic surfactant is important to achieve wetting and durable hydrophilicity. Preferably the ratio of ionic surfactant to non-ionic surfactant is 1:5 to 5:1 parts by weight and more preferably 1:4 to 4:1 parts by weight.

Suitable ionic surfactants include functional hydrophilic groups of sulfate, sulfonate, sultaine, phosphate and combinations thereof. As used herein an ionic "surfactant" is understood to mean a surfactant molecule having at least one hydrophilic functional groups (e.g. sulfate, sulfonate, sultaine, and phosphate groups) and at least one hydrophobic group such as an alkyl, alkylene, aralkyl or alkaryl group generally having 6 to about 30 carbon atoms (as an average carbon chain length). Examples include octadecylsulfate sodium salt, paraffin sulfonate salts, branched chain alkane sulfonate salts, dioctylsulfosuccinate sodium salt, dodecylbenzene sulfonate, lauryl phosphate, Ceteth-10 PPG-5 phosphate, and the like.

Suitable non-ionic surfactants include non-ionic, non-fluorinated, polyoxyethylene group-containing surfactants and non-ionic fluorochemical surfactants and combinations thereof. The non-ionic, nonfluorinated surfactants have from 1 to 100 moles of ethylene oxide per mole of hydrophobe and having at least one hydrophobic group such as an alkyl, alkylene, aralkyl or alkaryl group generally having 6 to about 30 carbon atoms. Preferred non-ionic nonfluorinated surfactants have from 1 to 20 moles of ethylene oxide per mole of hydrophobe and more preferably from 1 to 10 moles of ethylene oxide per mole of hydrophobe. Typically the alkylene oxide chain is connected to the hydrophobe through an ether or ester bond. Preferably, the one or more non-ionic, non-fluorinated, polyoxyethylene group-containing surfactants contain between 5 and 80 weight percent polyoxyethylene, more preferably 10 and 60 weight percent polyoxyethylene. Examples include steareth-2, steareth-10, beheneth-5, ethoxylates of eicosanol having 1-5 moles of ethylene oxide, as well as esters such as PEG 400 distearate, PEG 1000 distearate, PEG 600 monolaurate and the like.

Suitable non-ionic fluorinated surfactants include surfactants having perfluoroalkyl groups having at least 4 carbon atoms and a suitable nonionic hydrophilic group such as polyalkoxylates, and those described in U.S. Pat. Nos. 5,804,625 and 7,230,043. It is recognized by those skilled in the art that ethoxylates are often a distribution of ethoxylation levels. Thus, the wt % ethylene oxide or the number of moles of ethylene oxide discussed herein are average values. The wt % values are understood to be weight average values. Values expressing the moles of ethylene oxide per mole of alkanol or alkanoic acid are number average values.

Preferred porous fabric constructions of the fibers described herein produced as knits, wovens, and nonwovens have apparent surface energies greater than 60 dynes/cm, and preferably greater than 70 dynes/cm when tested by the Apparent Surface Energy Test disclosed in the Examples. Preferred porous fabric materials made from the durable hydrophilic fibers described herein wet with water, and thus have an apparent surface energy of greater than 72 dynes/cm (surface tension of pure water). Most preferred materials instantly absorb water and remain water absorbent after aging for 10 days at any of 5° C., 23° C. and 45° C. "Instant" absorption means a 100 µl drop of water that is gently placed (not dropped) on the fabric, and that does not form a discrete droplet on the surface of the fabric, but is absorbed into the pores.

Preferred film constructions of the present invention are wettable by aqueous fluids and have a contact angle with deionized water of less than 40 degrees, preferably less than 30 degrees, and most preferably less than 20 degrees when measured using a Tantec Contact Angle Meter (Shaumburg, Ill.) which is described as the half-angle technique in U.S. Pat. No. 5,268,733.

The present invention also discloses a method of making a relatively homogenous hydrophilic polymer composition comprising at least one ionic surfactant in an amount of at least 0.25, preferably at least 0.5%, even more preferably at least 0.75% by weight, and most preferably at least 1.0% by weight in order to get sufficient hydrophilicity and durability. The ionic surfactant(s) is preferably present in a concentration no greater than 8% by weight, preferably no greater than 6% by weight, even more preferably no greater than 4% by weight, and most preferably no greater than 2% by weight in order to prevent unnecessary degradation in physical properties, avoid foaming when challenged with aqueous fluids, and to prevent bond failures in laminated products. The compositions of the present invention also include at least one non-ionic surfactant in a concentration of at least 0.25%, preferably at least 0.5% even more preferably at least 0.75% by weight, and most preferably at least 1% by weight in order to obtain sufficient hydrophilicity and durability.

The ionic surfactant and non-ionic surfactant may be used in the final compositions by blending in a melt process with a polymer, and forming a film, fiber, or foam. These compositions may be also made, however, by first making a concentrate or "master batch" containing one or both surfactants at much higher concentrations. These concentrate(s) may be used to make the final compositions by blending the concentrate with additional polymer, and forming a film, fiber, or foam. In some instances the method may also include post heating the web to a temperature greater than 50° C. While not preferred, in some instances it may be desirable to add additional surfactant using a coating method to the surface of the fabric or film formed from the compositions described herein.

Polyolefin Polymers

Polyolefins are polymers useful in the compositions described herein. Examples include polyethylene; copolymers of ethylene with longer chain olefins; polypropylene; poly(1-butene); poly(3-methylbutene); poly(4-methylpentene); and copolymers of ethylene with propylene, 1-butene, 1-hexene, 1-octene, 1-decene, 4-methyl-1-pentene, and 1-octadecene, including linear and branched chain polyolefins and so called metallocene polyolefins.

Polyolefins as used herein also include copolymers of olefinic monomers with nonolefinic monomers. Representative monomers that are copolymerizable with the olefins include: vinyl ester monomers such as vinyl acetate, vinyl propionate, vinyl butyrate, vinyl chloroacetate, and vinyl chloropropionate; acrylic and alpha-alkyl acrylic acid monomers and their alkyl esters; amides and nitriles such as acrylic acid, methacrylic acid, ethacrylic acid, methyl acrylate, ethyl acrylate, N,N-dimethyl acrylamide, methacrylamide, and acrylonitrile; vinyl aryl monomers such as styrene, o-methoxystyrene, p-methoxystyrene, and vinyl naphthalene; vinyl and vinylidene halidemonomers such as vinyl chloride, vinylidene chloride, and vinylidene bromide; alkyl ester monomers of maleic and fumaric acid and anhydrides thereof such as dimethyl maleate, diethyl maleate, and maleic anhydride; vinyl alkyl ether monomers such as vinyl methyl ether, vinyl ethyl ether, vinyl isobutyl ether, and 2-chloroethyl vinyl ether; vinyl pyridine monomers; N-vinyl carbazole monomers; and N-vinyl pyrrolidine monomers. Other exemplary polyolefins include polyalphaolefins.

The preferred polyolefins used to produce the non-woven web or microporous film of the present invention is a poly(alpha)olefin consisting of repeating units derived from mono-1-olefins (alpha olefins) having 2 to 8 carbon atoms. The monomers that can be employed to produce the thermoplastic olefinic polymer for use in this invention include ethylene, propylene and 1-butene, alone, or in admixture, or in sequential polymerization systems. Examples of suitable thermoplastic polymers include polyethylene, polypropylene, propylene/ethylene copolymers, polybutylene and blends thereof, such as polypropylene/polybutylene blends. Most preferred is polypropylene. Processes for preparing these polymers are well known, and the invention is not limited to a polymer made with a particular catalyst or process.

Some embodiments of this invention comprise a two-component blend of polymers including at least one thermoplastic polymer and a second hydrophilic enhancing polymer which are then blended with the ionic and non-ionic surfactants. These embodiments have enhanced surface-modification, for example, increased hydrophilicity, compared to the thermoplastic polymer compositions with surfactant or two-component blends of only thermoplastic polyolefin polymer and hydrophilic enhancing polyolefin polymer. Polymers useful as the hydrophilic enhancing polyolefin polymer of this invention are those polymers (or blends of polymers) that reduce the crystallinity of the thermoplastic polymer. Generally, a hydrophilic enhancing polymer will not decrease the crystallinity of the thermoplastic polymer if it is incompatible with the thermoplastic polymer. While not intending to be bound by theory, we have found that such hydrophilic enhancing polymers can enhance the hydrophilicity, presumably by enabling more surfactant to get to the surface of the article and/or by ensuring proper orientation of the surfactant. Reduction in the degree of crystallinity of the polymer blend can be determined using differential scanning calorimetry (DSC).

For fiber formation the polyolefin polymer preferably has a relatively high melt flow index. Preferably the melt flow index is greater than 15 g/10 min, more preferably greater than 20 g/10 min., and most preferably greater than 25 g/10 min when measured according to ASTM D1238.

When the thermoplastic polymer is a polypropylene homopolymer, (for example Escorene™ PP3505 from Exxon), a copolymer, or mixtures thereof, the hydrophilic enhancing polymers useful in this invention include resins such as polybutylene and copolymers thereof; for example, polybutylene PB 0200, polybutylene PB 0400, polybutylene PB 0800, polybutylene DP 8310, and polybutylene DP 8340 (all available from Basell, Wilmington, Del.); and atactic poly(alpha)olefins, such as APAO-2180 E8 atactic polypropylene (high MW homopolymer of polypropylene, available from Rexene Co.).

The hydrophilic enhancing polymer, such as polybutylene PB 0400, generally is effective at levels of about at least 2 wt. %, with a preferred level of at least about 4 wt. %. The hydrophilic enhancement effect is seen at additive levels of up to 25 wt. % and higher, however, for some materials this may adversely impact other important physical properties such as tensile strength. In most embodiments the hydrophilic enhancing polymer is present at levels no more than 8 wt. %.

Surfactants

Compositions of the present invention include one or more surfactants to help wet the surface and/or to aid in contacting and killing microorganisms. As used herein the term "surfactant" means an amphiphile (a molecule possessing both polar and nonpolar regions which are covalently bound) capable of reducing the surface tension of water. The term is meant to include soaps, detergents, emulsifiers, surface active agents, and the like. Surfactants must have at least one polar group but may have more than one. Similarly, the surfactants must have at least one non-polar group but may have more than one.

Ionic Surfactants

Anionic Surfactants

Anionic surfactants useful in this invention include surfactants with the following structure:

$$R\text{—}(O)_x SO_3^- M^+$$

Where:

R=hydrocarbon C7-C30 alkyl or C7-C30 alkylene, a C4-C16 perfluorinated alkyl which is branched or straight chain, or C12-C30 aralkyl and may be optionally substituted with 0-100 alkylene oxide groups such as ethylene oxide, propylene oxide groups or a combination thereof in random or block arrangement, and may be further optionally substituted on or in the carbon chain with O, N, or S such as ester or ether linkages;

X=0 or 1; and

M=any salt; preferably alkali earth metal salts, preferably Li+, K+, or Na+, or amine salts including tertiary and quaternary amines.

Examples of anionic surfactants include C7-C18 alkane sulfonates, C7-C18 secondary alkane sulfonates, alkylbenzene sulfonates such as dodecylbenzene sulfonate; C7-C18 alkyl sulfates, alkylether sulfates such as sodium trideceth-4 sulfate, sodium laureth-4 sulfate, sodium laureth-8 sulfate (available from Stepan Company Northfield Ill.), docusate sodium (sodium dioctylsulfosuccinate) such as Complemix 100 available from Cytec, potassium perfluorooctylsulfonate, and the like. Also useful are zwitterionic sultaine surfactants having the following structure:

$$(R\text{—}O)2P(O)O^- M^+ \text{ or } R\text{—}OP(O)(O^-)2M^+_2$$

Where R and M are defined as above.

Examples include stearyl phosphate available as Sipostat 0018 from Specialty Industrial Products, Inc. of Spartanburg, S.C., laureth-4 phosphate, and dilaureth-4 phosphate.

Also useful are ammonium sulfonate amphoterics, a class of amphoteric surfactants often referred to as "sultaines" or "sulfobetaines," and can be represented by the following formula $$R^3\text{—}(C(O)\text{—}NH)_a\text{—}R^5\text{—}N^+(R^4)_2\text{—}R^6\text{—}SO_3^-$$

wherein $R^3$-$R^6$ and "a" are as described below.

$R^3$ is a (C1-C22)alkyl or alkylene group, preferably C6-C16 alkyl group.

$R^4$ is H or a (C1-C12)alkyl, alkylene group or a C6-C12 alkaryl or aralkyl group. $R^4$ is preferably a methyl or benzyl group and most preferably both $R^4$ groups are methyl groups. When $R^4$ is H it is understood that the surfactant at higher pH values could exist as a tertiary amine with a cationic counterion such as Na, K, Li, or a quaternary amine group.

$R^5$ and $R^6$ are each independently a (C1-C10)alkylene group that may be the same or different and may be optionally substituted with one or more N, O, or S atoms, or one or more hydroxyl or amine groups.

a=0 or 1.

Examples include cocamidopropylhydroxysultaine (commercially available as MACKAM 50-SB from McIntyre Group Ltd.), laurylamidopropyl hydroxy sultaine, tallowamidopropyl hydroxy sultaine, myristylamidopropyl hydroxy sultaine, and the like.

The surfactants having anionic functionality may have a metal or organic ammonium counterion. Certain useful anionic surfactants are selected from the group consisting of: sulfonates and sulfates such as alkyl sulfates, alkylether sulfates, alkyl sulfonates, alkylether sulfonates, alkylbenzene sulfonates, alkylbenzene ether sulfates, alkylsulfoacetates, secondary alkane sulfonates, secondary alkylsulfates, and the like. Many of these can be represented by the formulas:

$$R^7\text{—}(OCH_2CH_2)_n(OCH(CH_3)CH_2)_p\text{—}(Ph)_{a1}\text{-}(OCH_2CH_2)_m\text{—}(O)_b\text{—}SO_3^- M^+$$

and $$R^7\text{—}CH[SO_3\text{-}M^+]\text{-}R^8$$

wherein: a1 and b=0 or 1; n, p, and m=0-100 (preferably 0-20); $R^7$ is defined as below provided at least one of $R^7$ or $R^8$ is at least C8; $R^8$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n6" and "m3" groups) and propylene oxide groups (i.e., the "p2" groups) can occur in reverse order as well as in a random, sequential, or block arrangement. $R^7$ is R (as described above) or may be an alkylamide group such as $R^9$—C(O)N(CH$_3$)CH$_2$CH$_2$— as well as ester groups such as —OC(O)—CH$_2$—, wherein $R^9$ is a (C8-C22)alkyl group (branched, straight, or cyclic group). Examples include, but are not limited to: alkyl ether sulfonates, such as lauryl ether sulfates including POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17) secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo(C12-C16) fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries.

Suitable anionic surfactants also include phosphates such as alkyl phosphates, alkylether phosphates, aralkylphosphates, and aralkylether phosphates. Many may be represented by the formula:

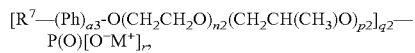

wherein: Ph, $R^7$, a3, n2, p2, and M are defined above; r is 0-2; and q2=1-3; with the proviso that when q2=1, r=2, and when q2=2, r=1, and when q2=3, r=0. As above, the ethylene oxide groups (i.e., the "n2" groups) and propylene oxide groups (i.e., the "p2" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J., and mixtures thereof.

The nonpolar R groups described herein are understood to represent a number average chain length. For example, many surfactants are derived from natural oils such as coconut oil which have a range of alkyl chain lengths. In the case of coconut oil this has been reported to vary from C8 to C16 with a number average length of about C12-C13.

One or more surfactants may be used in and/or on the compositions described herein at a suitable level to produce the desired result. In some embodiments, when used in the composition, they are present in a total amount of at least 0.5 wt-%, at least 0.75 wt-%, at least 1.0 wt-%, or at least 2.0 wt-%, based on the total weight of the composition. In certain embodiments, in which a very hydrophilic web is desired, or a web that can withstand multiple assaults with aqueous fluid, the surfactant component comprises greater than 2 wt. %, greater than 3 wt. %, or even greater than 5 wt. % of the polymer composition. For sheath core fibers, laminates, or other structures where the surfactant has not been added to the entire composition, the percentage values give above are the wt % surfactant in the layer or element to which the surfactant(s) has been added.

In other embodiments, the surfactants are present in a total amount of no greater than 15 wt-%, no greater than 10 wt-%, no greater than 8 wt-%, or no greater than 6 wt-%, based on the total weight of the fabric, film, or foam composition. For sheath core fibers, laminates, or other structures where the surfactant has not been added to the entire composition the values give above are the wt % surfactant in the layer or element to which the surfactant(s) has been added.

For melt processing, preferred surfactant components have low volatility and do not decompose appreciably under process conditions. The preferred surfactants contain less than 10 wt. % water, preferably less than 5% water, and more preferably less than 2 wt. % and even more preferably less than 1% water (determined by Karl Fischer analysis). Moisture content may be kept low in order to prevent hydrolysis of the polymer or other hydrolytically sensitive compounds in the composition, which will help to give clarity to extruded films or fibers.

It may be particularly convenient to use a surfactant predissolved in a non-volatile carrier. The carrier is typically thermally stable and can resist chemical breakdown at processing temperatures which may be as high as 150° C., 180° C., 200° C. or even as high as 250° C. In a preferred embodiment, the surfactant carrier is a liquid at 23° C. Preferred carriers include polyalkylene oxides such as polyethylene glycol, polypropylene glycol, random and block copolymers of ethylene oxide and propylene oxide, thermally stable polyhydric alcohols such as propylene glycol, glycerin, polyglycerin, and the like. The polyalkylene oxides may be linear or branched depending on the initiating polyol. For example, a polyethylene glycol initiated using ethylene glycol would be linear while one initiated with glycerin, trimethylolpropane, or pentaerythritol would be branched.

Preferred carriers also may include low molecular weight esters of polyhydric alcohols such as triacetin, glyceryl caprylate/caprate, acetyltributylcitrate, and the like. Carriers also may include lower molecular weight polymers. For example, the concentrates may be made in lower MW polyethylene or polypropylene.

Non-Ionic Surfactants
Non-Ionic, Non-Fluorinated Surfactants

The non-ionic hydrocarbon surfactant(s) of this invention are characterized by one of the following formulas:

R-PA or R-PA-R

Where each R is defined above and PA is a polyalkoxylate such as polyethylene oxide or a random or block copolymer of ethylene oxide and propylene oxide having 0-100 moles of alkoxylate per mole of R. Preferably PA is polyethylene glycol. The length of the polyethylene glycol chain is selected such that the average weight % PEG in the surfactant is 5 to 60%, preferably 10-40%. Note that R may be connected to the PA group through an ether, ester, amide, or amine bond. The PA may be terminated in –OH or in a R group having 1-22 carbon atoms. Preferably PA is terminated in OH. Examples include: Brij™ alkyl and alkylene ethoxylates and Triton™ X-nonylphenol and octylphenol ethoxylates. Note that for low ethoxylation level surfactants, some of the starting alcohol may be present (n=0) in the composition. The starting alcohol is included when calculating the average number of ethylene oxide units per mole of hydrophobe.

The non-ionic hydrocarbon surfactant(s) of this invention also may include a surfactant of the following formula:

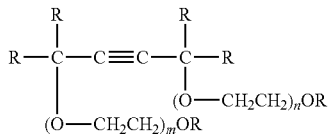

wherein: n and m are numbers between 1 and about 100 preferably 1 to about 20 and are chosen such that the weight percent of polyoxyethylene in the surfactant is on average between 5 and 80 weight percent, preferably 10 and 60 weight %. In calculating the wt % the average amount of polyethylene oxide is determined by gas or liquid chromatography together with mass spectrometry and is taken as the weight average. Each R is selected independently from one another as an alkyl or an aryl group that may be substituted or unsubstituted and that contain from 2 to about 20 carbon atoms whose skeletal chain may be straight-chained, branched, or, if sufficiently large, cyclic, or any combination thereof such skeletal chain can also optionally include one or more catenary heteroatoms such as oxygen, hexavalent sulfur, and trivalent nitrogen atoms bonded to the carbon atoms of the skeletal chain.

Examples include the Surfynol and Dynol surfactants available from Air Products, Allentown, Pa.

Non-Ionic Fluorochemical Surfactants

The perfluorinated radical containing surfactants suitable in this invention are those described in U.S. Pat. Nos. 5,804,625 and 7,230,043 as well as non-ionic Zonyl surfactants available from Dupont. Anionic perfluorinated radical-containing surfactants, such as Zonyl surfactants available from Dupont, can be used as the ionic surfactant, discussed above.

Particularly useful non-ionic fluorochemical surfactants include fluoroaliphatic group-containing non-ionic compounds that contain one or more blocks of water-solubilizing polyoxyalkylene groups in their structures. A class of such surfactants is described in U.S. Pat. No. 5,300,357 (Gardiner), whose descriptions are incorporated herein by reference. Generally, the fluorochemical surfactants useful in the invention include those represented below by Formula I.

$(R_f\text{-}Q)_n\text{-}Z$ (I)

wherein:

$R_f$ is a fluoroaliphatic group having at least 4 fully-fluorinated carbon atoms that may be straight-chained, branched, or, if sufficiently large, cyclic, or any combination thereof. The skeletal chain in the fluoroaliphatic radical can include one or more catenary heteroatoms, such as oxygen, hexavalent sulfur, and trivalent nitrogen atoms bonded only to carbon atoms of the skeletal chain. Fully fluorinated fluoroaliphatic groups are preferred, but hydrogen or chlorine atoms may be present as substituents provided that not more than one atom of either if present for every two carbon atoms. While $R_f$ can contain a large number of carbon atoms, compounds where $R_f$ is not more than 20 carbon atoms will be preferred since larger radicals usually represent a less efficient utilization of the fluorine than is possible with shorter chains. Fluoroaliphatic radicals containing from about 3 to about 12 carbon atoms are most preferred. Generally, $R_f$ will contain between about 40 and about 78 weight percent fluorine. The terminal portion of the $R_f$ group preferably contains at least four fully fluorinated carbon atoms, e.g., $CF_3CF_2CF_2CF_2$— and particularly preferred compounds are those in which the $R_f$ group is fully or substantially completely fluorinated, as in the case where $R_f$ is a perfluoroalkyl, e.g., $CF_3(CF_2)_n$—. Suitable $R_f$ groups include, for example, $C_4F_9$—, $C_3F_7$—, and $C_5F_{11}$—, $C_8F_{17}$—, $C_6F_{13}CH_2CH_2$—, and $C_{10}F_{21}$—$CH_2CH_2$—.

Q in Formula I above is a multivalent, generally divalent, linking group, or is a covalent bond, that provides a means to link $R_f$ with the depicted group Z, which is a non-ionic, water-solubilizing group; Q can comprise a heteroatom-containing group, e.g., a group such as —S—, —O—, —CO—, —SO_2—, —N(R)— (where R is a hydrogen or a $C_1$ to $C_6$ substituted or unsubstituted alkyl group that may comprise a catenary heteroatom such as O, N, S), —$C_nH_{2n}$— (n=1 to 6); Q can comprise a combination of such groups such as would give, for example, —CON(R) $C_nH_{2n}$—, —$SO_2N(R)C_nH_{2n}$—, —$SO_3C_6H_4N(R)C_nH_{2n}$—, —$SO_2N(R)C_nH_{2n}O[CH_2CH(CH_2Cl)O]_gCH_2CH(CH_2Cl)$— (n=1 to 6; g=1 to 10), —$SO_2N(CH_3)C_2H_4OCH_2CH(OH)$ $CH_2$—, —$SO_2N(C_2H_5)C_2H_4OCH_2CH(OH)CH_2$, —$SO_2N$ $(H)CH_2CH(OH)CH_2NHC(CH_3)CH_2$—, —$(CH_2)_2$ $S(CH_2)_2$—, and —$(CH_2)_4SCH(CH_3)CH_2$—;

Z in Formula I above is a non-ionic, water-solubilizing group comprising a poly(oxyalkylene) group, $(OR')_x$, where R' is an alkylene group having from 2 to about 4 carbon atoms, such as —$CH_2CH_2$—, —$CH_2CH_2CH_2$—, —CH $(CH_3)CH_2$—, and —$CH(CH_3)CH(CH_3)$—, and x is a number between about 2 and about 20; Z preferably contains a poly(oxyethylene) group. The oxyalkylene units in said poly(oxyalkylene) being the same, such as in poly(oxypropylene), or present as a mixture, such as in a heteric straight or branched chain of randomly distributed oxyethylene and oxypropylene units i.e., poly(oxyethylene-co-oxypropylene), or as in a straight or branched chain blocks of oxypropylene units. The poly(oxyalkylene) chain can be interrupted by or include one or more catenary linkages such as where Z includes a group of the formula

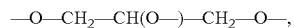

providing such linkages do not substantially alter the water-solubilizing character of the poly(oxyalkylene) chain. The Z group may be terminated with a hydroxyl, lower alkyl ether, alkaryl ether, or fluoroalkyl ether, for example, —$OCH_3$, —$OCH_2CH_3$, —$OC_6H_4C(CH_3)_2CH_2C(CH_3)_2CH_3$, —$OC_6H_4(C_9H_{19})_2$, —$OC_{12}H_{25}$, —$OC_{14}H_{29}$, —$OC_{16}H_{33}$, or —O-$QR_f$ (where Q and $R_f$ are as defined supra); and n is a number from 1 to 6.

Fluoroaliphatic group-containing non-ionic surfactants, including those depicted above by Formula I, may be prepared using known methods including those methods described in U.S. Pat. No. 2,915,554 (Albrecht et al.). The Albrecht patent discloses the preparation of fluoroaliphatic group-containing non-ionic compounds from active hydrogen-containing fluorochemical intermediates, such as fluoroaliphatic alcohols (e.g., $R_fC_2H_4OH$), acids (e.g., $R_fSO_2N$ $(R)CH_2CO_2H$), and sulfonamides (e.g., $R_fSO_2N(R)H$) by reaction of the intermediates with, for example, ethylene oxide to yield, respectively, $R_fC_2H_4(OC_2H_4)_nOH$, $R_fSO_2N$ $(R)CH_2CO_2(C_2H_4O)_nH$, and $R_fSO_2N(R)(C_2H_4O)_nH$, where n is a number greater than about 3 and R is a hydrogen or a lower alkyl group (e.g., from 1 to 6 carbon atoms). Analogous compounds may be prepared by treating the intermediate with propylene oxide. The fluoroaliphatic oligomers disclosed in U.S. Pat. No. 3,787,351 (Olson), and certain fluorinated alcohol-ethylene oxide condensates described in U.S. Pat. No. 2,723,999 (Cowen et al.), whose descriptions are incorporated herein by reference, are also considered useful. Fluoroaliphatic group-containing non-ionic surfactants containing hydrophobic long-chain hydrocarbon groups may be prepared by reacting a fluoroaliphatic epoxide, such as

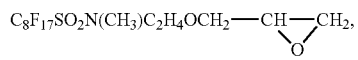

with, for example, an ethoxylated alkylphenol or alcohol, such as $CH_3C(CH_3)_2CH_2C(CH_3)_2C_6H_4(OC_2H_4)_{9.5}OH$ or $C_{12}H_{25}(OC_2H_4)_9OH$, respectively in the presence of $BF_3$ etherate. They may also be prepared by first converting the ethoxylated alkylphenol or alcohol to a chloride by reaction with thionyl chloride, then reacting the resulting chloride with a fluoroaliphatic sulfonamide containing an active hydrogen, for example $C_8F_{17}SO_2NH(CH_3)$, in the presence of sodium carbonate and potassium iodide.

Specific examples of non-ionic fluorochemical additives for use in the invention include: $C_3F_7SO_2N(C_2H_5)(CH_2CH_2O)_xC_8H_{17}$, $C_3F_7SO_2N(CH_3)(CH_2CH_2O)_xC_8H_{17}$, $C_4F_9SO_2N(C_2H_5)(CH_2CH_2O)_xC_8H_{17}$, $C_4F_9SO_2N(CH_3)(CH_2CH_2O)_xC_8H_{17}$, $C_4F_9SO_2N(CH_3)(CH_2CH_2O)_xCH[CH_2CH(CH_3)_2][CH_2CH(CH_3)CH_2CH(CH_3)_2]$, $C_4F_9SO_2N(C_2H_5)(CH_2CH_2O)_xCH[CH_2CH(CH_3)_2][CH_2CH(CH_3)CH_2CH(CH_3)_2]$, $C_3F_7SO_2N(CH_3)(CH_2CH_2O)_xCH[CH_2CH(CH_3)_2][CH_2CH(CH_3)CH_2CH(CH_3)_2]$, $C_5F_{11}SO_2N(CH_3)(CH_2CH_2O)_xCH[CH_2CH(CH_3)_2][CH_2CH(CH_3)CH_2CH(CH_3)_2]$, $C_5F_{11}SO_2N(CH_3)(CH_2CH_2O)_xC_{10}H_{21}$, $C_4F_9SO_2N(CH_3)(CH_2CH_2O)_xC_6$—$H_4$—$C(CH_3)_2$—$CH_2$—$C(CH_3)_3$, $C_5F_{11}SO_2N(CH_3)(CH_2CH_2O)_xC_{14}H_{29}$, $C_3F_7SO_2N(CH_3)(CH_2CH_2O)_xC_6$—$H_4$—$C_8$—$H_{17}$, $C_4F_9SO_2N(CH_3)CH_2CH(OH)CH_2O(CH_2CH_2O)_xC_6H_4C(CH_3)_2$—$CH_2$—$C(CH_3)_3$, $C_4F_9SO_2N(CH_3)CH_2CH(OH)CH_2O(CH_2CH_2O)_xCH[CH_2CH(CH_3)_2][CH_2CH(CH_3)CH_2CH(CH_3)_2]$, and $C_4F_9SO_2N(CH_3)(CH_2CH_2O)_xC(O)$—$C_{11}H_{23}$, wherein x for each of the above compounds is 8-15.

The compounds of Formula I provide durable hydrophilicity to the polymer composition, and advantageously are generally more thermally stable than other polymer additives, including homologous compounds having longer (e.g. $C_8F_{17}$—) perfluoroalkyl groups. While not being bound, it is believed that that compounds like those of Formula I, but having shorter $R_f$ groups, are generally less thermally stable than those having $R_f$ groups as defined. Further, it has been discovered that compounds of Formula I, having $C_3$-$C_5$ fluoroalkyl groups, provide performance comparable to or better than those having longer flouoralkyl groups, e.g. perfluoroctyl groups. As described further herein, $C_3$-$C_5$ perfluoroalkyl groups are more cost-effective and more environmentally favorable.

Optional Components

Other optional components may be included in the compositions described herein.

An antimicrobial component may be added to impart antimicrobial activity to the compositions. The antimicrobial component is that component of the composition that provides at least part of the antimicrobial activity, i.e., it has at least some antimicrobial activity for at least one microorganism. It is preferably present in a large enough quantity to be leached from the composition and kill bacteria. It may also be biodegradable and/or made or derived from renewable resources such as plants or plant products. Biodegradable antimicrobial components can include at least one functional linkage such as an ester or amide linkage that can be hydrolytically or enzymatically degraded.

Examples of antimicrobial components suitable for use in the present invention include those described in Applicants' co-pending application, U.S. Patent Application Publication No. 2008-0142023-A1, and incorporated by reference herein in its entirety.

Certain antimicrobial components are uncharged and have an alkyl or alkenyl hydrocarbon chain containing at least 7 carbon atoms. For melt processing, preferred antimicrobial components have low volatility and do not decompose under process conditions. The preferred antimicrobial components contain less than 2 wt. % water, and more preferably less than 0.10 wt. % (determined by Karl Fischer analysis). Moisture content is kept low in order to prevent off gassing or "gels" and to give clarity to extruded film.

When used, the antimicrobial component content (as it is ready to use) is typically at least 1 wt. %, 2 wt. %, 5 wt. %, 10 wt. % and sometimes greater than 15 wt. %. In certain embodiments, in which a low strength is desired, the antimicrobial component comprises greater than 20 wt. %, greater than 25 wt. %, or even greater than 30 wt. % of the composition.

Certain antimicrobial components are amphiphiles and may be surface active. For example, certain antimicrobial alkyl monoglycerides are surface active. For certain embodiments of the invention that include antimicrobial components, the antimicrobial component is considered distinct from a surfactant component. See, for example, applicants copending U.S. Patent Application Publication No. 2004-0241216-A1 which is incorporated herein by reference. As taught in this reference the compositions may further comprise enhancers such as alphahydroxyacids and the like. Alkyl monoglyceryl ethers also are possible such as Sensiva SC50 (2-ethylhexylglyceryl ether, INCI name ethylhexyglycerin) available from Schulke Mayr, Belgium, N.V.

The compositions may further comprise organic and inorganic fillers. For implantable applications biodegradable, resorbable, or bioerodible inorganic fillers may be particularly appealing. These materials may help to control the degradation rate of the polymer composition. For example, many calcium salts and phosphate salts may be suitable. Exemplary biocompatible resorbable fillers include calcium carbonate, calcium sulfate, calcium phosphate, calcium sodium phosphates, calcium potassium phosphates, tetracalcium phosphate, .alpha.-tricalcium phosphate, beta-tricalcium phosphate, calcium phosphate apatite, octacalcium phosphate, dicalcium phosphate, calcium carbonate, calcium oxide, calcium hydroxide, calcium sulfate dihydrate, calcium sulfate hemihydrate, calcium fluoride, calcium citrate, magnesium oxide, and magnesium hydroxide. A particularly suitable filler is tribasic calcium phosphate (hydroxy apatite).

Other additional components include antioxidant, colorant such as dyes and/or pigments, antistatic agents, fluorescent brightening agents, odor control agents, perfumes and fragrances, active ingredients to promote wound healing or other dermatological activity, combinations thereof and the like.

Applications and Methods of Manufacturing

Articles comprising the inventive composition may be made by processes known in the art for making polymer sheets from polymer resins. For many applications, such articles can be placed in water at 23° C. without substantial loss of physical integrity (e.g. tensile strength) after being immersed 2 hours and dried. Typically, these articles contain little or no water. The water content in the article after extruding, injection molding or solvent casting is typically less than 10% by weight, preferably less than 5% by weight, more preferably less than 1% by weight and most preferably less than 0.2% by weight. Polymeric sheets may be formed by an extrusion process from the inventive resin compositions described herein, resulting in hydrophilic polymer sheets useful in applications such as medical drapes and garments, personal care items, personal hygiene items, wound absorbents, tape backings, and food wrapping.

Articles that may be made of the inventive composition may include medical drapes and gowns, including surgical drapes, procedural drapes, plastic specialty drapes, incise drapes, barrier drapes, barrier gowns, spunbond/melt blown/ spunbond (SMS or SMMS) gowns, and the like, wound dressings, wound absorbents, wound contact layers, surgical sponges use to absorb blood and body fluids during surgery, surgical implants, as well as tubular extrusion products such as vascular catheters, urinary catheters, endrotracheal tubes, shunts, wound drains and other medical devices.

Importantly the preferred hydrophilic additive surfactants of the present invention allow for adhesive, thermal, and/or ultrasonic bonding of fabrics and films made thereof. Articles made of the compositions described herein may be thermally or ultrasonically welded together as well as being welded to other compatible articles. The compositions may be used in conjunction with other materials to form constructions such as sheath/core materials, laminates, compound structures of two or more materials, or useful as coatings on various medical devices. The compositions of may also be useful in the fabrication of surgical drapes, medical articles, diaper components such as top sheets, components for feminine hygiene pads, cosmetic and home wipes, surgical sponges, wound dressings, and the like.

The compositions described herein are particularly suitable for use in surgical drapes and gowns due to their unique wetting properties. For example, the polyolefin/surfactant compositions have durable hydrophilicity as described herein. Non-woven webs, films and sheets comprising the compositions have good tensile strength; can be heat sealed to form strong bonds allowing specialty drape fabrication; which can be important in disposable products; and can have high surface energy to allow wettability and fluid absorbency. In the case of non-wovens, surface energy is measured for nonwovens using the Apparent Surface Energy test described below. For films, surface energy is measured by contact angles with distilled water often are less than 50 degrees, preferably less than 30 degrees, and most preferably less than 20 degrees when measured on a flat film using the half angle technique described in U.S. Pat. No. 5,268,733 and a Tantec Contact Angle Meter, Model CAM-micro, Schamberg, Ill. In order to determine the contact angle of compositions in a form other than films, a film of the composition should be made by solvent casting.

It is believed that such non-woven, film and tube materials can be sterilized by ethylene oxide gas without significant loss of physical strength (tensile strength for a 1 mil thick film does not decrease by more than 20% and preferably by not more than 10% after exposure to a standard 50° C. (warm) ethylene oxide sterilization cycle with includes 3 evacuations prior to EO gas injection and 3 exhaust evacuation cycles to remove the residual ethylene oxide.

The hydrophilic characteristic of the compositions may improve articles such as wound and surgical dressings and tapes by improving absorbency. If the composition is used in a wound dressing backing film, the film may be partially (e.g. zone or pattern) coated or completely coated with various adhesives, including but not limited to pressure sensitive adhesives (PSAs), such as acrylic and block copolymer adhesives, hydrogel adhesives, hydrocolloid adhesives, and foamed adhesives. PSAs can have a relatively high moisture vapor transmission rate to allow for moisture evaporation.

Suitable pressure sensitive adhesives include those based on acrylates, polyurethanes, KRATON and other block copolymers, silicones, rubber based adhesives as well as combinations of these adhesives. The preferred PSAs are the normal adhesives that are applied to skin such as the acrylate copolymers described in U.S. Pat. No. RE 24,906, the disclosure of which is hereby incorporated by reference, particularly a 97:3 iso-octyl acrylate:acrylamide copolymer. Also preferred is an 70:15:15 isooctyl acrylate-ethyleneoxide acrylate:acrylic acid terpolymer, as described in U.S. Pat. No. 4,737,410 (Example 31), the disclosure of which is hereby incorporated by reference. Other useful adhesives are described in U.S. Pat. Nos. 3,389,827, 4,112,213, 4,310,509 and 4,323,557, the disclosures of which are hereby incorporated by reference. Inclusion of medicaments or antimicrobial agents in the adhesive is also contemplated, as described in U.S. Pat. Nos. 4,310,509 and 4,323,557.

Other medical devices that may be made, in whole or in part, of the inventive composition include: sutures, suture fasteners, surgical mesh, slings, and other medical devices.

In many applications the films, fibers, or nonwovens of the present invention have essentially no adhesion to themselves (i.e. they do not block together). In fact, it is important when making articles that are folded such as surgical drapes that the articles unfold easily after prolonged contact of the various layers. These layers must be easily unfolded. Preferably the layers unfold with no noticeable adhesion at all between 2 layers of the present invention after sitting overnight under a load of 0.7 kg/cm$^2$.

The compositions of the present invention may also be useful in consumer hygiene products, such as adult incontinence, infant diapers, feminine hygiene products, and others as described in Applicants' co-pending application, U.S. Patent Application Publication No. 2008-0200890-A1, and incorporated by reference herein in its entirety.

In one process for making the inventive composition, the thermoplastic polymer in a melt form is mixed in a sufficient amount relative to the surfactant to yield a polymer composition having hydrophilic characteristics as described herein. A variety of equipment and techniques are known in the art for melt processing polymeric compositions. Such equipment and techniques are disclosed, for example, in U.S. Pat. No. 3,565,985 (Schrenk et al.), U.S. Pat. No. 5,427,842 (Bland et. al.), U.S. Pat. Nos. 5,589,122 and 5,599,602 (Leonard), and U.S. Pat. No. 5,660,922 (Henidge et al.). Examples of melt processing equipment include, but are not limited to, extruders (single and twin screw), Banbury mixers, and Brabender extruders for melt processing the inventive composition.

The ingredients of the composition may be mixed in and conveyed through an extruder to yield a polymer composition, preferably without polymer degradation or side reactions in the melt. The processing temperature is sufficient to mix the aliphatic polyester and surfactant, and allow extruding the composition as a film or fiber. Potential degradation reactions include transesterification, hydrolysis, chain scission and radical chain decomposition, and process conditions should minimize such reactions. The composition has properties that are desirable in applications such as food wrap, e.g., transparent (not hazy) and being free of oily residue on the surface (which might indicate phase separation of components from the polymer matrix).

The invention will be further clarified by the following examples which are exemplary and not intended to limit the scope of the invention.

EXAMPLES

Apparent Surface Energy Test Method:

The method for measuring the surface energy is AATCC Test Method 118-1983, with the modifications described below. Surface energies measured according to this modified test method are hereinafter referred to as "apparent" surface energies. AATCC test method 118-1983 determines the surface energy of a fabric by evaluating the fabric's resistance to wetting by a series of selected hydrocarbon compositions. The hydrocarbons set forth in AATCC 118-1983, however, only provide for measurements of surface energy from about 19.8 to 27.3 dynes per centimeter at 25° C. This range is extended by employing various mixtures of methanol and water in the fabric resistance test. The compositions and their representative surface tensions are presented in Table 1.

TABLE 1

| Liquid No. | Volume % Methanol/Water | Surface Tension (dynes/cm at |
|---|---|---|
| 7 | 65/45 | 30 |
| 8 | 53/47 | 35 |
| 9 | 40/60 | 40 |
| 10 | 25/75 | 45 |
| 11 | 21/79 | 50 |
| 12 | 15/85 | 55 |
| 13 | 8.5/91.5 | 60 |

The test procedure is as follows. A specimen of the example material is placed flat on a smooth, horizontal surface. Using the method of AATCC 118-1983 except that beginning with the lowest number test liquid, 5 drops of the liquid (approximately 100 microliters) are placed gently (not dropped) on the surface of the example material. If at least three of the five drops wick into the fabric within 60 seconds, the liquid of the next higher surface energy is used. When at least 3 drops remain on the example fabric surface the apparent surface tension is recorded as the lowest surface tension fluid that had at least 3 drops not absorb. More precisely the apparent surface energy can be reported as a range between the highest number that had all drops absorb and the lowest number that held out at least 3 of the drops.

Preferred materials used in the compositions described herein wet with water and thus have an apparent surface energy of greater than 72 dynes/cm (surface tension of pure water). The most preferred materials instantly absorb water and remain water absorbent after aging for 10 days at 5° C., 23° C. and 45° C. More preferred materials instantly absorb water and remain water absorbent after aging for 20 days at 5° C., 23° C. and 45° C. Even more preferred materials instantly absorb water and remain water absorbent after aging for 30 days at 5° C., 23° C. and 45° C.

Control Examples 1-5

Spunbond type nonwoven examples were prepared using the masterbatches blended with neat polypropylene. The polypropylene used is indicated below. The masterbatch materials were dried prior to use.

The spunbond nonwovens were obtained using a Davis-Standard BLUE RIBBON (DS-25®) extruder (Davis Standard Corporation, Pawcatuck, Conn.) using a 2.5 inch (63.5 mm 3:1 compression ratio barrier flight single screw extruder to feed through a pump to an extrusion head including multiple die orifices.

The die head had a total of 512 orifice holes with a throughput of 0.50 g/hole/min (33.83 lb/hr). The die had a transverse length of 7.875 inches (200 mm). The hole diameter was 0.020 inch (0.445 mm) and L/D ratio of 6. The melt extrusion temperature at the die of the neat polypropylene was set at 235° C., while the melt extrusion temperature of polypropylene with the additives was dependent on the type and amount of additives. The temperature was adjusted in order to make similar webs to the control (pure polypropylene). A representative description of the web forming and bonding process is exemplified by U.S. Patent Application Publication No. 2008/0038976 A1, and incorporated herein as reference in its entirety. Control Examples 1-5 were prepared with the following components: polypropylene supplied from Exxon Mobile PP3155 (Lot #5J2281B4, having a melt index of 36 g/10 min measured according to ASTM D1238); polybutylene supplied from Bassel Polyolefins DP8911 (Lot #FK09XX501); Hostastat HS1 FF supplied as Masterbatch Material #105190, from Clariant Corp., Charlotte N.C., C10-C18 secondary alkane sulfonate sodium salt, antistat supplied as a concentrate in polypropylene, 20% by weight surfactant; FC surfactant FCS-1 as described in U.S. Pat. No. 7,230,043; and TPM 12713 hydrophilic melt additive, supplied from Masterbatch Techmer PM, analyzed and found to be nominally about 30% solids in polypropylene with the following composition =R—O(CH2CH2O)nH where R=C20H23 (1-eicosanol and n=0-5 having the following distribution shown in Table 2.

TABLE 2

| Compound | Weight % |
|---|---|
| Eicosanol | 10.0 |
| eicosanol + 1 EO | 6.2 |
| eicosanol + 2 EO | 4.9 |
| eicosanol + 3 EO | 3.3 |
| eicosanol + 4 EO | 2.0 |
| eicosanol + 5 EO | 1.4 |
| Total | 27.8 |

Thus, the average wt % PEG in this surfactant is 15.3% which is derived as shown below in Table 3.

TABLE 3

| N | % PEG | Wt % of total nonionic surfactant | % EO | Weighted Ave. % EO |
|---|---|---|---|---|
| 0 | 10.0 | 36.0 | 0.0 | 0.0 |
| 1 | 6.2 | 22.3 | 12.9 | 2.9 |
| 2 | 4.9 | 17.6 | 22.8 | 4.0 |
| 3 | 3.3 | 11.9 | 30.7 | 3.6 |
| 4 | 2.0 | 7.2 | 37.1 | 2.7 |
| 5 | 1.4 | 5.0 | 42.5 | 2.1 |
| Total | 27.8 | 100.0 | | 15.3 |

TABLE 4

Use of TPM 12713 R-PEG surfactant alone

| Control Examples % TPM 12713 | | Control 1 0% | Control 2 1% | Control 3 2% | Control 4 4% | Control 5 4% with hot air bonding |
|---|---|---|---|---|---|---|
| 60° C. 24 hrs | H | 28 | 28 | 28 | 30 | 30 |
| 60° C. 24 hrs | L | 30 | 30 | 30 | 33 | 33 |
| Humidity 24 hrs | H | 28 | 28 | 30 | 30 | 28 |
| Humidity 24 hrs | L | 30 | 30 | 33 | 33 | 30 |
| 48 hrs after production | H | 28 | 28 | 28 | 33 | 39 |
| 48 hrs after production | L | 30 | 30 | 30 | 36 | 42 |
| 72 hrs after production | H | 28 | 28 | 28 | 33 | 50 |
| 72 hrs after production | L | 30 | 30 | 30 | 36 | 55 |
| 96 hrs after production | H | 28 | 28 | 30 | 33 | 50 |
| 96 hrs after production | L | 30 | 30 | 33 | 36 | 55 |

H = Highest Surface Energy Wetting (Highest number to wet out)
L = Lowest Surface Energy Non-Wetting (Lowest number not to wet out)
("Humidity" = 40 C/75% relative humidity recirculated chamber where samples were aged.)

The data shows that the nonwoven materials made using up to 4% TPM12713 (an eicosanol ethoxylate in a polyethylene carrier) were not able to absorb water. The results of Control 5 indicate that through air bonding the web in line with hot air appeared to increase the surface energy substantially but this Control 5 still would not absorb water.

Examples 6-14

The raw materials listed in Examples 1-5 were used to make the compositions listed in Table 5, according to the procedure of Examples 1-5. Table 5 also describes the initial wetting results obtained using water on the roll as it was winding up. Only Examples 8, 10, 12-14 showed instantaneous wet out on the machine as it was being produced.

TABLE 5

Use of TPM 12713 R-PEG in Combination with Polybutylene and R-SO3 Surfactant

| Ex. | Techmer 12713 (Wt %) | Hostastat HS1 (Wt %) | Poly-butylene (Wt %) | FCS-1, (Wt. %) | Initial Water Wetting Results: |
|---|---|---|---|---|---|
| 6 | 4 | 0 | 4 | 0 | No wetting. |
| 7 | 4 | 4 | 4 | 0 | Some absorbent spots. |
| 8 | 4 | 4 | 6 | 0 | Very rapid, spontaneous wetting. |
| 9 | 0 | 4 | 6 | 0 | No spontaneous wetting on roll; repellent. |
| 10 | 2 | 4 | 6 | 0 | Very rapid, spontaneous wetting. |
| 11 | 4 | 0 | 8 | 0 | Does not wet well on roll. |
| 12 | 0 | 4 | 4 | 2 | Instantaneous wetting on roll. Very absorbent. |
| 13 | 4 | 6 | 0 | 0 | Some absorbency on roll. After a few hours it wets with great absorbency. |
| 14 | 0 | 4 | 0 | 2 | Wets out very well on roll and post. |

The webs produced were tested for Apparent Surface Energy as a function of time at 5° C., 23° C. (room temperature), and 45° C. The nonwoven webs were stored in these conditions in sealed but porous poly/Tyvek pouches. Samples were removed periodically and allowed to come to room temperature for 1 day prior to testing. All the data is included in Tables 6A-8B. Note that samples were taken from the beginning and end of the rolls produced.

TABLE 6A

Apparent Surface Energy Results after Aging at Room Temperature

| Days @ RT Aging | # | * | Example 6 4% Tech/ 4% PB | Example 7 4% Tech/ 4% HS/ 4% PB | Example 8 4% Tech/ 4% HS/ 6% PB | Example 9 4% HS/ 6% PB | Example 10 2% Tech/ 4% HS/ 6% PB |
|---|---|---|---|---|---|---|---|
| 1 Day | — | H | 30 | 50 | 72 | 30 | 72 |
| 1 Day | — | L | 33 | 55 | N/A | 33 | N/A |
| 4 Days | O | H | 30 | 72 | 72 | 30 | 36 |
| 4 Days | O | L | 33 | — | — | 33 | 39 |
| 4 Days | I | H | 30 | 72 | 72 | 30 | 36 |
| 4 Days | I | L | 33 | — | — | 33 | 39 |
| 5 Days | O | H | 30 | 55 | 72 | 30 | 36 |
| 5 Days | O | L | 33 | 72 | — | 33 | 39 |
| 5 Days | I | H | 30 | 55 | 72 | 30 | 36 |
| 5 Days | I | L | 33 | 72 | — | 33 | 39 |
| 11 Days | O | H | 33 | 55 | 50 | 30 | 39 |
| 11 Days | O | L | 36 | 72 | 55 | 33 | 42 |
| 11 Days | I | H | 33 | 55 | 55 | 30 | 39 |
| 11 Days | I | L | 36 | 72 | 72 | 33 | 72 |
| 53 Days | O | H | 30 | 55 | 47 | 30 | 39 |
| 53 Days | O | L | 33 | 72 | 50 | 33 | 42 |
| 53 Days | I | H | 30 | 50 | 50 | 30 | 39 |
| 53 Days | I | L | 33 | 55 | 55 | 33 | 42 |

I = Inside of Roll
O = Outside of Roll
* H = Highest Surface Energy Wetting (Highest number to wet out)
* L = Lowest Surface Energy Non-Wetting (Lowest number not to wet out)
HS = Hostastat HS1 FF masterbatch
Tech = Techmer 12713 masterbatch
PB = polybutylene, Bassel Polyolefins DP8911

TABLE 6B

Apparent Surface Energy Results after Aging at Room Temperature

| Days @ RT Aging | # | * | Example 11 4% Tech/ 8% PB | Example 12 4% HS/ 4% PB/ 2% FC | Example 13 4% Tech/ 6% HS | Example 14 4% HS/ 2% FC |
|---|---|---|---|---|---|---|
| 1 Day | — | H | No sample | 72^ | 72^ | 72^ |
| 1 Day | — | L | No sample | N/A | N/A | N/A |
| 4 Days | O | H | 39 | 72^ | 72^ | 72^ |
| 4 Days | O | L | 42 | N/A | N/A | N/A |
| 4 Days | I | H | 36 | 72^ | 72^ | 72^ |
| 4 Days | I | L | 39 | N/A | N/A | N/A |
| 5 Days | O | H | 39 | 72^ | 72^ | 72^ |
| 5 Days | O | L | 42 | N/A | N/A | N/A |
| 5 Days | I | H | 39 | 72^ | 72^ | 72^ |
| 5 Days | I | L | 42 | N/A | N/A | N/A |
| 11 Days | O | H | 50 | 72^ | 72^ | 72^ |
| 11 Days | O | L | 55 | N/A | N/A | N/A |
| 11 Days | I | H | 47 | 72^ | 72^ | 72^ |
| 11 Days | I | L | 50 | N/A | N/A | N/A |
| 53 Days | O | H | 45 | 72^ | 72^ | 72^ |
| 53 Days | O | L | 47 | N/A | N/A | N/A |
| 53 Days | I | H | 45 | 72^ | 72^ | 72^ |
| 53 Days | I | L | 47 | N/A | N/A | N/A |

I = Inside of Roll
O = Outside of Roll
* H = Highest Surface Energy Wetting (Highest number to wet out)
* L = Lowest Surface Energy Non-Wetting (Lowest number not to wet out)

Examples results shown as "72^" that the apparent surface energy is greater than 72 dyne/cm (i.e. water wet the sample and no higher surface tension liquid was used). "N/A" indicates that the sample was wetted by water, thus all lower surface energies would wet as well.

After 11 days of ambient laboratory storage, samples of Examples 6-14 were stored under controlled conditions of 5° C., 23° C. and 45° C., and then periodically tested. Test results are shown in Tables 7A, 7B, 8A and 8B; in addition to the "53 days" result shown in Tables 6A and 6B.

TABLE 7A

Apparent Surface Energy Results after Aging at 45° C.

| Days @ 45° C. | Example 6 4% Tech/ 4% PB | Example 7 4% Tech/ 4% HS/ 4% PB | Example 8 4% Tech/ 4% HS/ 6% PB | Example 9 4% HS/ 6% PB | Example 10 2% Tech/ 4% HS/ 6% PB |
|---|---|---|---|---|---|
| 0 Day | 33 | 55 | 50 | 30 | 39 |
| 1 Day | 42 | 30 | 30 | 30 | 33 |
| 7 Days | 72 | 28 | 30 | 30 | 33 |
| 14 Days | 72 | 30 | 28 | 30 | 33 |
| 28 Days | 39 | 30 | 28 | 30 | 30 |
| 42 Days | 30 | 28 | 28 | 30 | 30 |

TABLE 7B

Apparent Surface Energy Results after Aging at 45° C.

| Days @ 45° C. | Example 11 4% Tech/ 8% PB | Example 12 4% HS/ 4% PB/ 2% FC | Example 13 4% Tech/ 6% HS | Example 14 4% HS/ 2% FC |
|---|---|---|---|---|
| 0 Day | 50 | 72^ | 72 | 72^ |
| 1 Day | 72^ | 72^ | 45 | 72^ |
| 7 Days | 72^ | 72^ | 39 | 72^ |
| 14 Days | 72^ | 72^ | 33 | 45 |
| 28 Days | 72^ | 72^ | 33 | 36 |
| 42 Days | 72^ | 50 | 33 | 39 |

Examples results shown as "72^", indicate Examples which wet out immediately with water.

TABLE 8A

Apparent Surface Energy Results after Aging at 5° C.

| Days @ 5° C. | Example 6 4% Tech/ 4% PB | Example 7 4% Tech/ 4% HS/ 4% PB | Example 8 4% Tech/ 4% HS/ 6% PB | Example 9 4% HS/ 6% PB | Example 10 2% Tech/ 4% HS/ 6% PB |
|---|---|---|---|---|---|
| 0 Day | 33 | 55 | 50 | 30 | 39 |
| 1 Day | 33 | 55 | 55 | 30 | 39 |
| 7 Days | 33 | 72^ | 72^ | 30 | 39 |
| 14 Days | 33 | 55 | 72^ | 30 | 42 |
| 28 Days | 33 | 55 | 55 | 30 | 42 |
| 42 Days | 33 | 55 | 55 | 30 | 42 |

TABLE 8B

Apparent Surface Energy Results after Aging at 5° C.

| Days @ 5° C. | Example 11 4% Tech/ 8% PB | Example 12 4% HS/ 4% PB/ 2% FC | Example 13 4% Tech/ 6% HS | Example 14 4% HS/ 2% FC |
|---|---|---|---|---|
| 0 Day | 50 | 72^ | 72^ | 72^ |
| 1 Day | 50 | 72^ | 72^ | 72^ |
| 7 Days | 55 | 72^ | 72^ | 72^ |
| 14 Days | 55 | 72^ | 72^ | 72^ |
| 28 Days | 50 | 72^ | 72^ | 72^ |
| 42 Days | 47 | 72^ | 72^ | 72^ |

Examples results shown as "72^", indicate Examples which wet out immediately with deionized water.

Figure 2:
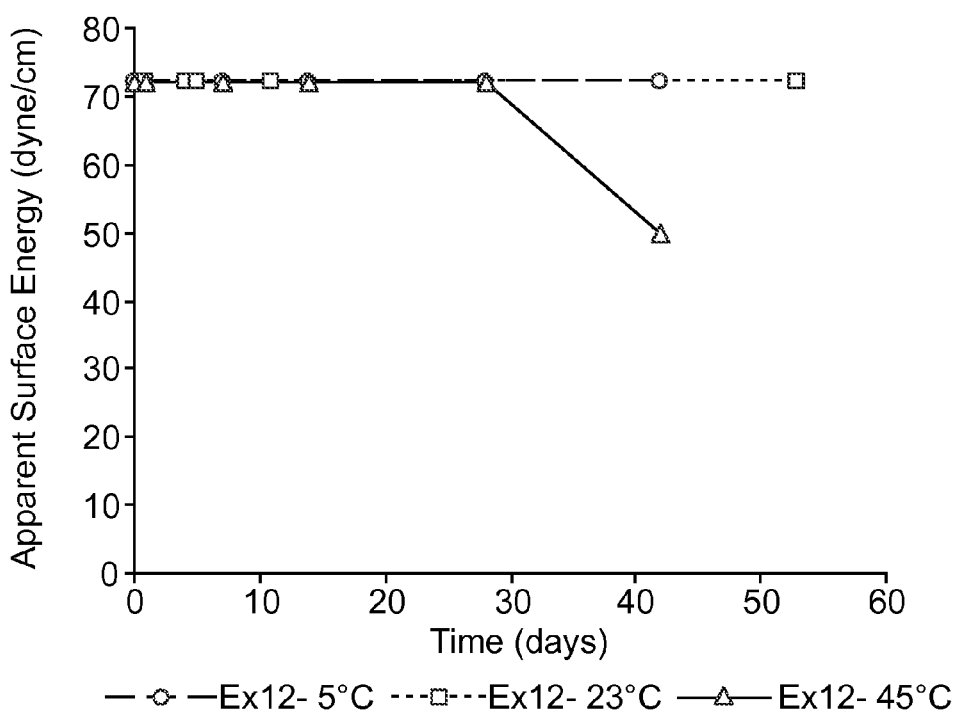
FIG. 2 is a graph that shows the data for apparent surface energy of another exemplary nonwoven composition as described herein.
Figure 3:
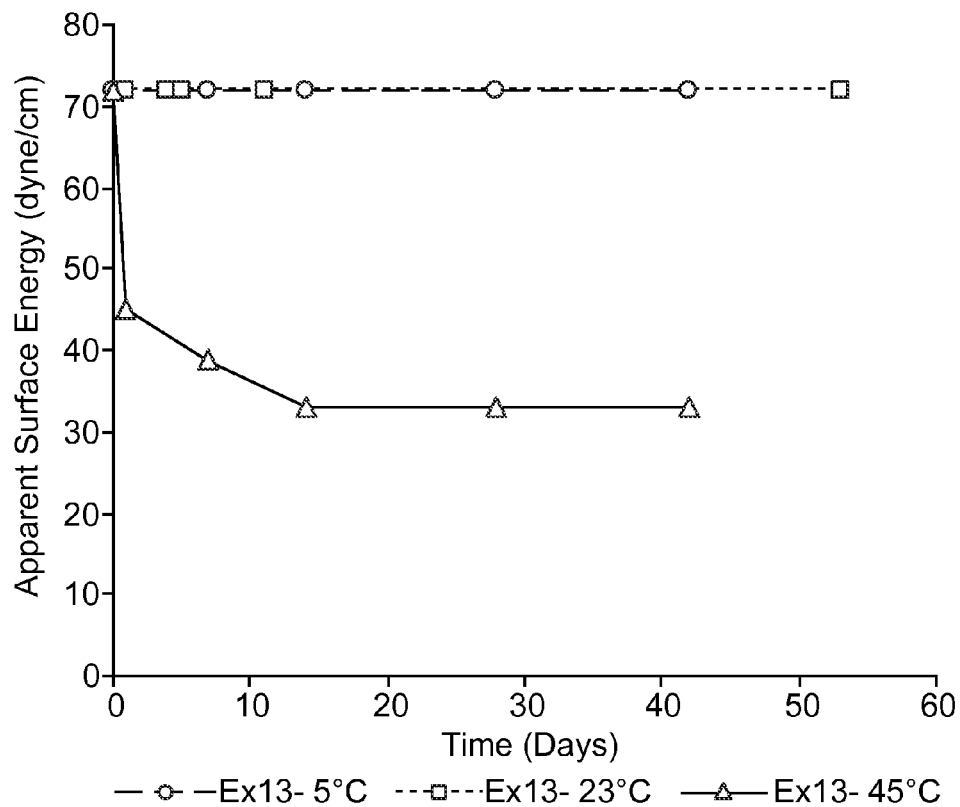
FIG. 3 is a graph that shows the data for apparent surface energy of another exemplary nonwoven composition as described herein.
Figure 4:
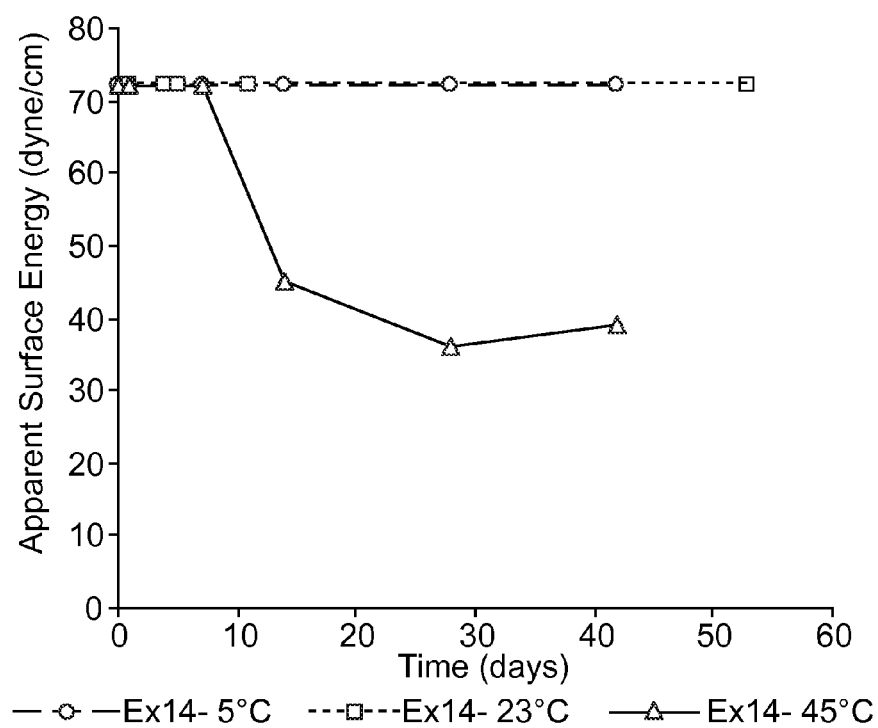
FIG. 4 is a graph that shows the data for apparent surface energy of another exemplary nonwoven composition as described herein.

The results are also plotted in FIGS. 1-4 for the compositions in Examples 11, 12, 13, and 14.

The complete disclosures of the patents, patent documents and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A thermoplastic composition comprising:
   a) a thermoplastic polyolefin polymer;
   b) at least one ionic surfactant selected from the group consisting of:
      (i) sulfates; and
      (ii) sulfonates;
   c) at least one non-ionic, non-fluorinated, polyoxyalkylene group-containing surfactant that contains between 5 and 80 weight percent polyoxyalkylene;
   wherein the composition is free of fluorochemical surfactants;
   wherein the ionic surfactant is present at 0.5-4 weight percent of the composition and the non-ionic, non-fluorinated, polyoxyalkylene group-containing surfactant is present at 0.5-4 weight percent of the composition;

wherein a mixture of the surfactants (b) and (c) is homogeneously incorporated in the thermoplastic polyolefin polymer of the composition; and wherein the composition is in the form of fibers, which form a fabric that is instantaneously water absorbent when a 100 μl drop of water that is gently placed (not dropped) on the fabric, and that does not form a discrete droplet on the surface of the fabric, but is absorbed into the pores.

2. The composition of claim 1, wherein the thermoplastic polyolefin polymer is derived from monomers having less than or equal to 8 carbon atoms.

3. The composition of claim 1, wherein the thermoplastic polyolefin polymer is a poly(alpha-olefin).

4. The composition of claim 1, wherein the thermoplastic polyolefin polymer comprises polypropylene.

5. The composition of claim 1, wherein the ionic surfactant comprises at least one nonpolar group selected from the group consisting of a C7-C30 branched or straight chain alkyl group, C7-C30 branched or straight chain alkylene group, and a C12-C30 aralkyl group.

6. The composition of claim 1, wherein the non-ionic, non-fluorinated, polyoxyethylene group-containing surfactant contain between 10 and 60 weight percent polyoxyethylene.

7. The composition of claim 1, wherein the non-ionic, non-fluorinated, polyoxyalkylene group-containing surfactant has at least one hydrophobic group having 6 to 30 carbon atoms.

8. The composition of claim 1, wherein the composition further comprises a hydrophilic enhancing polyolefin derived from monomers having at least 4 hydrocarbons.

9. The composition of claim 1, wherein the hydrophilic enhancing polyolefin has a molecular weight less than that of the thermoplastic polyolefin polymer.

10. The composition of claim 1, further comprising an antimicrobial component.

11. The composition of claim 1, wherein the composition is melt processable.

12. An article comprising the composition of claim 1, said article being selected from woven webs, nonwoven webs, and combinations thereof.

13. The article of claim 1, wherein the article is a nonwoven web selected from the group consisting of a spunbond web, a blown microfiber web, or a hydroentangled web.

14. The article of claim 1, wherein the article is a surgical drape, a surgical gown, a wound contact material, or a personal hygiene article.

* * * * *

UNITED STATES PATENT AND TRADEMARK OFFICE
CERTIFICATE OF CORRECTION

PATENT NO. : 9,777,407 B2
APPLICATION NO. : 13/260589
DATED : October 3, 2017
INVENTOR(S) : Scholz et al.

It is certified that error appears in the above-identified patent and that said Letters Patent is hereby corrected as shown below:

On the Title Page

Item (54), and in the Specification, Column 1, Line 1, Title, delete "POLYPROYLENE" and insert -- POLYPROPYLENE --, therefor.

In the Specification

<u>Column 17</u>
Line 21, delete "endrotracheal" and insert -- endotracheal --, therefor.

Signed and Sealed this
First Day of May, 2018

Andrei Iancu
*Director of the United States Patent and Trademark Office*